US006372898B1

(12) United States Patent
Cacalano et al.

(10) Patent No.: US 6,372,898 B1
(45) Date of Patent: *Apr. 16, 2002

(54) HUMAN JAK3 VARIANTS

(75) Inventors: Nicholas A. Cacalano, San Francisco; James A. Johnston, Los Gatos, both of CA (US)

(73) Assignee: Schering Corporation, Kenilworth, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/191,786

(22) Filed: Nov. 13, 1998

(51) Int. Cl.$^7$ .......................... C07H 21/04; C12N 9/12; C12N 1/20; C12N 15/00; C12N 5/00

(52) U.S. Cl. .................. 536/23.1; 435/194; 435/320.1; 435/325; 435/252.3

(58) Field of Search ............................. 435/325, 252.3, 435/194, 320.1, 69.1; 536/23.1, 23.2

(56) References Cited

U.S. PATENT DOCUMENTS 5,837,448 A * 11/1998 Lemke et al. ................... 435/6

OTHER PUBLICATIONS

Dana P. Ascherman, et al., *J. Biol. Chem.*, 272(13):8704–8709, Mar. 28, 1997. "Interleukin–2 (IL–2)–mediated Induction of the IL–2 Receptor α Chain Gene".

Min Chen, et al., *Proc. Natl. Acad. Sci.*, 94:6910–6915, Jun. 1997. "The amino terminus of JAK3 is necessary and sufficient for binding to the common γ chain and confers the ability to transmit interleukin 2–mediated signals".

R. J. Duhe, and W. L. Farrar. *J. Interferon and Cytokine Research*, 18:1–15, 1998. "Structural and Mechanistic Aspects of Janus Kinases: How the Two–Faced God Wields a Double–Edged Sword".

David M. Heery, et al., *Nature*, 387:733–736, Jun. 12, 1997. "A signature motif in transcription co–activators mediates binding to nuclear receptors".

Warren J. Leonard, and John J. O'Shea. *Annu. Rev. Immunol.*, 16:293–322, 1998. "JAKS and Stats: Biological Implications".

Paolo Maachi, et al., *Nature*, 377:65–68, Sep. 7, 1995. "Mutations of Jak–3 gene in patients with autosomal severe combined immune deficiency (SCID)".

Jennifer M. Puck, et al., *Immunol. Today*, 17:507–511,1996. "IL2RGbase: a database of γc–chain defects causing human X–SCID".

M. C. Riedy, et al., *GenBank*, Accession No. U70065, Jan. 28, 1997. Description: "Human JAK3 gene, complete cds".

M. C. Riedy, et al., *Genomics*, 37:57–61, 1996. "Genomic Sequence, Organization, and Chromosomal Localization of Human JAK3".

Sarah M. Russell, et al., *Science*, 266:1042–1045, Nov. 11, 1994. "Interaction of IL–2Rβ and γ$_c$ Chains with Jak1 and Jak3: Implications for XSCID and XCID".

* cited by examiner

*Primary Examiner*—Rebecca E. Prouty
*Assistant Examiner*—M. Monshipouri
(74) *Attorney, Agent, or Firm*—Hugh Wang; Edwin P. Ching

(57) ABSTRACT

Muteins are provided, which are mutational variants of human Jak3 proteins. Particular positions of natural proteins are identified as critical in providing various different activities. Specific embodiments demonstrate properties of variations at these positions.

10 Claims, No Drawings

HUMAN JAK3 VARIANTS

FIELD OF THE INVENTION

The present invention relates to the field of biology, e.g., describing compositions which interact in cell signaling. The invention provides various compositions and methods directed to protein interactions occurring in the signal transduction pathway, e.g., compositions which include variants of human Jak3, a protein exhibiting tyrosine kinase-like structure, and which functions in regulating intracellular signaling. In particular, it provides agonists and/or antagonists of said proteins.

BACKGROUND OF THE INVENTION

Cytokines are molecules that mediate differentiation or other signals typically between the circulating cell components of the mammalian circulatory system. Cytokines function through receptors, many of which have been characterized. See, e.g., Aggarwal and Gutterman (eds. 1991) *Human Cytokines: Handbook for Basic and Clinical Research*, Blackwell, Oxford.

Binding of cytokines to their receptors induces a cascade of intracellular signaling events that results in increased tyrosine phosphorylation of specific target proteins, and initiates a program of altered gene expression and proliferation. See e.g., Leonard and O'Shea (1998) *Annu. Rev. Immunol.* 16:293–322. Cytokine receptors typically lack intrinsic tyrosine kinase activity and signal via non-receptor tyrosine kinases of the Jak family that associate with the cytoplasmic domains of receptor chains. The paradigm for ligand-induced signaling is that trans-phosphorylation and activation of receptor-associated Jak kinases occurs upon ligand dependent receptor subunit aggregation. These activated kinases phosphorylate tyrosine residues of the receptor chain subunits, providing docking sites for src-homology (SH2) domains of signal transducers and activators of transcription (STATs), as well as other signaling molecules, e.g., the adapter molecule Shc. STATs are recruited to the phosphorylated receptor, where they are phosphorylated. This allows them to dimerize, translocate to the nucleus, and stimulate the expression of cytokine-inducible genes. While the general model for cytokine-induced signaling has been elucidated, the molecular details of the association of Jak family members with the cytoplasmic domains of receptor chains are not understood.

The functional receptors for the cytokines IL-2, IL-4, IL-7, IL-9, and IL-15 all utilize the common gamma chain ($\gamma_c$) signaling subunit. The importance of signaling through $\gamma_c$ is underscored by the fact that specific mutations in either the $\gamma_c$ or the Janus kinase that interacts with it, Jak3, result in phenotypically similar Severe Combined Immunodeficiency (SCID). Infants with SCID suffer from severe infections due to reduced levels of T and natural killer (NK) cells, as well as hypogammaglobulinemia. Current preferred treatment typically requires heterologous bone marrow transplantation to replace lost T and NK cell functions.

The Jak family of kinases consists of four known mammalian homologs, each consisting of 1100–1200 amino acids organized into seven Janus homology (JH) domains, based on sequence similarity among the family members. They do not possess classic SH2 or SH3 domains, and, except for the catalytic domains, exhibit little homology to other protein tyrosine kinases (PTKs).

As the IL-2 signaling complex is essential for T cell proliferation and is critically dependent on Jak3 activity, understanding this interaction would be a benefit in effecting processes involving, e.g., graft rejection, rheumatoid arthritis, and autoimmune or inflammatory diseases. The availability of agonists and antagonists to cytokine receptor signaling such as, e.g., IL-2, IL-4, IL-7, IL-9, IL-13, and IL-15 will be used to modulate these processes. The present invention provides these, as well as other proteins, useful, e.g., in determining the structure and mechanisms of immune regulation in a cell via the tyrosine kinases of the JAK family.

SUMMARY OF THE INVENTION

The present invention provides compositions that serve as an agonist or antagonist for Jak3 proteins. These agonists and antagonists will be useful in modulating T cell proliferation, and may be important in other hematopoietic or immunological function. In certain circumstances, these molecules will also have in vitro or in vivo therapeutic effects.

The present invention is based, in part, upon a structural analysis of a Jak3 mutation from a patient with autosomal severe combined immunodeficiency disease (SCID).

The mutation is a single amino acid substitution, Y100C, located in Janus homology domain 7 (JH7) that prevents kinase-receptor interaction and also results in a loss of IL-2-induced signaling in B-cells.

In particular, this insight leads to recognition of which specific amino acid residues of Jak3 kinase bind to the IL-2 receptor beta (IL-2Rβ) and common gamma ($\gamma_c$) chains, respectively, and initiate biochemical signals critical in controlling immune responses. Additionally, this information, leads to recognition of a region around the Jak3 Y100C mutation which has the ability to interact with $\gamma_c$ specifically the proline rich box1 region of the IL-2 receptor. Furthermore, a Jak3/Jak1 chimeric composition containing this region mediates IL-2 responses. This invention embraces natural ligands, e.g., specific mutations (muteins) of the natural sequences, fusion proteins, and chemical mimetics. It is also directed to DNAs encoding such variant proteins. Various uses of these different protein or nucleic acid compositions are also provided.

The present invention provides a polypeptide that: comprises at least three non-overlapping fragments of at least 17 contiguous amino acids selected from residues 70–193 of SEQ ID NO: 2 (human Jak3); interferes with the interaction of a human Jak3 with a human γ common receptor chain; and lacks any 8 contiguous amino acid residue fragment of SEQ ID NO: 1 residues 1–69 and 193–1124. Incertain embodiments: the interaction of the Jak3 with the human $\gamma_c$ is determined in a binding assay; the total number of residues of the three fragments is between 55 and 123; the polypeptide is selected from: residues 1–193, 70–193, 1–130, 70–130, or 70–256 of human Jak3; or a residue corresponding to position 98, 99, 100, or 102 of the Jake polypeptide is substituted, either singly or in combination.

In other embodiments, the invention provides a isolated polynucleotide encoding the described polypeptide, or its complement, including variants resulting from the degeneracy of the genetic code or point mutations. Preferably, the variants encode the same activity of the polypeptide; or the polynucleotide is operably linked to a replication or transcription sequence. Also provided is a cell transfected with the polynucleotide. Methods are provided, e.g., comprising screening a library comprising such polypeptides for a polypeptide that interferes with the interaction of a Jak3 with a $\gamma_c$, and identifying those polypeptides which do interfere. In certain embodiments, the screening is inside a cell.

Alternatively, the invention provides a polypeptide that: comprises a sequence matching at least 45 out of 53 of residues 263–315 of SEQ ID NO: 2 (human $\gamma_c$); comprises an amino acid residue substitution corresponding to position 266 and/or 269; and interferes with the interaction of human Jak3 with a human $\gamma_c$. Typically:

out of 53; the polypeptide comprises sequence corresponding to residues 263–269; or the residue at position 266 or 269 is substituted with a conservative substitution.

Nucleic acid embodiments include, e.g., an isolated polynucleotide encoding the described polypeptide, or its complement, including variants resulting from the degeneracy of the genetic code or point mutations. Typically, the variants encode the same activity of the polypeptide; or the polynucleotide is operably linked to a replication or transcription sequence. Cells transfected with the described polynucleotide are provided.

The invention provides methods, e.g., comprising screening a library comprising described polypeptides for a polypeptide that interferes with the interaction of a Jak3 with a $\gamma_c$, and identifying those polypeptides which do interfere. Often, the screening is inside a cell.

Yet another embodiment is a method of screening comprising screening a library of compositions for a candidate composition that blocks the interaction of a JH7/JH6 fragment of Jak3 with a box1/box2 fragment of $\gamma_c$. In certain embodiments, the JH7/JH6 fragment of Jak3 interacts specifically with residues 263–315 of human $\gamma_c$; or the box1/box2 fragment of $\gamma_c$ interacts specifically with residues 1–193 of human Jak3. Preferably, at least one of the fragments is: a recombinant or synthetic polypeptide; attached to a solid substrate; or detectably labeled. Other embodiments include those where the JH7/JH6 fragment of Jak3 is from human; or the box1/box2 fragment of $\gamma_c$ is from human. Preferred embodiments include where the Jak3 from human has a sequence of SEQ ID NO: 1; or the $\gamma_c$ from human has a sequence of SEQ ID NO: 2.

DETAILED DESCRIPTION OF THE PREFERRED EMBODIMENTS

OUTLINE

I. General
II. Agonists; antagonists
III. Physical Variants
   A. fragments
   B. post-translational variants
     1. glycosylation
     2. others
   C. species variants
IV. Nucleic Acids
   A. mutated natural isolates; methods
   B. synthetic genes
   C. methods to isolate
V. Antibodies
   A. polyclonal
   B. monoclonal
   C. fragments, binding compositions
VI. Making Agonists and Antagonists
   A. recombinant methods
   B. synthetic methods
   C. natural purification
VII. Uses
   A. diagnostic
   B. therapeutic
VIII. Kits
   A. nucleic acid reagents
   B. protein reagents
   C. antibody reagents

I. General

The present invention is based, in part, on a structural and mutational analysis of the interaction of Jak3 with cytokine receptor subunit binding sites. In one aspect, the present invention defines minimal regions sufficient to permit interaction between Jak3 and the common gamma chain of the cytokine receptor ($\gamma_c$).

The cytokines IL-2, IL-4, IL-7, IL-9, and IL-15 all bind to a common gamma chain ($\gamma_c$) signaling subunit shared among these various cytokine receptors. The importance of signaling through $\gamma_c$ is underscored by the fact that specific mutations in either $\gamma_c$ or the Jak3 kinase that interacts with it can produce a resulting disease states phenotypically reminiscent to Severe Combined Immunodeficiency (SCID).

In one aspect the present invention identifies a region of Jak3, including portions of JH6 and JH7, that is sufficient for kinase-receptor contact. It is also demonstrated herein that a Jak3 segment which overlaps two Janus homology domains, JH7 and JH6, defines a region sufficient for Jak3 interaction with the box1 region of $\gamma_c$ and for the functional interaction of Jak3 with an IL-2 receptor complex.

TABLE 1

Amino acid sequence (see SEQ ID NO: 1) of a primate, e.g., human, Jak3 (See also, e.g., GenBank Accession Numbers 400048, 2494714, 729281; and 461904). Complementary nucleic acid sequences and fragments are also contemplated.

```
(xi) SEQUENCE DESCRIPTION: SEQ ID NO:1:
Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
                20                  25                  30

Arg Ala Pro Gly Pro Pro Gln Arg Leu Ser Phe Ser Phe Gly Asp His
            35                  40                  45

Leu Ala Glu Asp Leu Cys Val Gln Ala Ala Lys Ala Ser Gly Ile Leu
        50                  55                  60

Pro Val Tyr His Ser Leu Phe Ala Leu Ala Thr Glu Asp Leu Ser Cys
65                  70                  75                  80
```

TABLE 1-continued

```
Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
               100                 105                 110

Glu Lys Cys His Arg Phe Gly Leu Arg Lys Asp Leu Ala Ser Ala Ile
           115                 120                 125

Leu Asp Leu Pro Val Leu Glu His Leu Phe Ala Gln His Arg Ser Asp
        130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
                180                 185                 190

Cys Leu Pro Pro Ser Leu Arg Asp Leu Ile Gln Gly Leu Ser Phe Val
                195                 200                 205

Thr Arg Arg Ala Ile Arg Arg Thr Val Arg Arg Ala Leu Pro Arg Val
        210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
                260                 265                 270

Val Ala Gly Asp Gly Gly Ile Ala Trp Thr Gln Gly Glu Gln Glu Val
            275                 280                 285

Leu Gln Pro Phe Cys Asp Phe Pro Glu Ile Val Asp Ile Ser Ile Lys
        290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
            340                 345                 350

Thr Asp Ser Gln His Phe Phe Cys Lys Glu Val Ala Pro Pro Arg Leu
            355                 360                 365

Leu Glu Glu Val Ala Glu Gln Cys His Gly Pro Ile Thr Leu Asp Phe
        370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
            420                 425                 430

Ser Pro Thr Gly Thr Phe Leu Leu Val Gly Leu Ser Arg Pro His Ser
            435                 440                 445

Ser Leu Arg Glu Leu Leu Ala Thr Cys Trp Asp Gly Gly Leu His Val
        450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495
```

TABLE 1-continued

```
Ser Ser Leu Val Gln Pro Gln Ser Gln Tyr Gln Leu Ser Gln Met Thr
            500             505             510

Phe His Lys Ile Pro Ala Asp Ser Leu Glu Trp His Glu Asn Leu Gly
            515             520             525

His Gly Ser Phe Thr Lys Ile Tyr Arg Gly Cys Arg His Glu Val Val
            530             535             540

Asp Gly Glu Ala Arg Lys Thr Glu Val Leu Leu Lys Val Met Asp Ala
545             550             555             560

Lys His Lys Asn Cys Met Glu Ser Phe Leu Glu Ala Ala Ser Leu Met
                565             570             575

Ser Gln Val Ser Tyr Arg His Leu Val Leu Leu His Gly Val Cys Met
            580             585             590

Ala Gly Asp Ser Thr Met Val Gln Glu Phe Val His Leu Gly Ala Ile
            595             600             605

Asp Met Tyr Leu Arg Lys Arg Gly His Leu Val Pro Ala Ser Trp Lys
            610             615             620

Leu Gln Val Val Lys Gln Leu Ala Tyr Ala Leu Asn Tyr Leu Glu Asp
625             630             635             640

Lys Gly Leu Pro His Gly Asn Val Ser Ala Arg Lys Val Leu Leu Ala
                645             650             655

Arg Glu Gly Ala Asp Gly Ser Pro Pro Phe Ile Lys Leu Ser Asp Pro
            660             665             670

Gly Val Ser Pro Ala Val Leu Ser Leu Glu Met Leu Thr Asp Arg Ile
            675             680             685

Pro Trp Val ALa Pro Glu Cys Leu Arg Glu Ala Gln Thr Leu Ser Leu
            690             695             700

Glu Ala Asp Lys Trp Gly Phe Gly Ala Thr Val Trp Glu Val Phe Ser
705             710             715             720

Gly Val Thr Met Pro Ile Ser Ala Leu Asp Pro Ala Lys Lys Leu Gln
                725             730             735

Phe Tyr Glu Asp Arg Gln Gln Leu Pro Ala Pro Lys Trp Thr Glu Leu
            740             745             750

Ala Leu Leu Ile Gln Gln Cys Met Ala Tyr Glu Pro Val Gln Arg Pro
            755             760             765

Ser Phe Arg Ala Val Ile Arg Asp Leu Asn Ser Leu Ile Ser Ser Asp
            770             775             780

Tyr Glu Leu Leu Ser Asp Pro Thr Pro Gly Ala Leu Ala Pro Arg Asp
785             790             795             800

Gly Leu Trp Asn Gly Ala Gln Leu Tyr Ala Cys Gln Asp Pro Thr Ile
                805             810             815

Phe Glu Glu Arg His Leu Lys Tyr Ile Ser Gln Leu Gly Lys Gly Asn
            820             825             830

Phe Gly Ser Val Glu Leu Cys Arg Tyr Asp Pro Leu Ala His Asn Thr
            835             840             845

Gly Ala Leu Val Ala Val Lys Gln Leu Gln His Ser Gly Pro Asp Gln
            850             855             860

Gln Arg Asp Phe Gln Arg Glu Ile Gln Ile Leu Lys Ala Leu His Ser
865             870             875             880

Asp Phe Ile Val Lys Tyr Arg Gly Val Ser Tyr Gly Pro Gly Arg Pro
                885             890             895

Glu Leu Arg Leu Val Met Glu Tyr Leu Pro Ser Gly Cys Leu Arg Asp
            900             905             910
```

TABLE 1-continued

```
Phe Leu Gln Arg His Arg Ala Arg Leu Asp Ala Ser Arg Leu Leu Leu
            915                 920                 925

Tyr Ser Ser Gln Ile Cys Lys Gly Met Glu Tyr Leu Gly Ser Arg Arg
            930                 935             940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
                965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
            995                 1000                1005

Asp Val Trp Ser Phe Gly Val Val Leu Tyr Glu Leu Phe Thr Tyr Cys
            1010                1015                1020

Asp Lys Ser Cys Ser Pro Ser Ala Glu Phe Leu Arg Met Met Gly Cys
1025                1030                1035                1040

Glu Arg Asp Val Pro Ala Leu Cys Arg Leu Leu Glu Leu Leu Glu Glu
                1045                1050                1055

Gly Gln Arg Leu Pro Ala Pro Pro Ala Cys Pro Ala Glu Val His Glu
            1060                1065                1070

Leu Met Lys Leu Cys Trp Ala Pro Ser Pro Gln Asp Arg Pro Ser Phe
            1075                1080                1085

Ser Ala Leu Gly Pro Gln Leu Asp Met Leu Trp Ser Gly Ser Arg Gly
            1090                1095                1100

Cys Glu Thr His Ala Phe Thr Ala His Pro Glu Gly Lys His His Ser
1105                1110                1115                1120

Leu Ser Phe Ser
```

Amino acid sequence (see SEQ ID NO: 2) of a primate, e.g., human, cytokine receptor common gamma chain (See also e.g., GenBank Accession Numbers 400048, 2494714, 729281, and 461904). Complementary nucleic acid sequences and fragments are also contemplated.

Note: the numbering system used herein does not include the first 23 amino residues of SEQ ID NO:2 as these residues represent a leader sequence for this cytokine receptor gamma common chain. Thus, amino residue 23 of SEQ ID NO:2 is referred to herein as amino residue 1 and so on for the remaining consecutive residues of the sequence. However, one can easily translate between any amino residue number as used herein and its equivalent in SEQ ID NO:2 or vice versa, simply by subtracting or adding the value 22 from any particular residue, e.g., in the "Example Section" herein, a proline amino acid of the gamma common chain is numbered as residue 266 the equivalent proline residue in SEQ ID NO:2 is residue number 288.

```
(xi) SEQUENCE DESCRIPTION: SEQ ID NO:2:
Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
            35                  40                  45

Ser Leu Ser Val Ser Thr Leu Pro Leu Pro Glu Val Gln Cys Phe Val
            50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
            85                  90                  95
```

TABLE 1-continued

```
Asp Lys Val Gln Lys Cys Ser His Tyr Leu Phe Ser Glu Glu Ile Thr
            100             105             110

Ser Gly Cys Gln Leu Gln Lys Lys Glu Ile His Leu Tyr Gln Thr Phe
            115             120             125

Val Val Gln Leu Gln Asp Pro Arg Glu Pro Arg Arg Gln Ala Thr Gln
    130             135             140

Met Leu Lys Leu Gln Asn Leu Val Ile Pro Trp Ala Pro Glu Asn Leu
145             150             155             160

Thr Leu His Lys Leu Ser Glu Ser Gln Leu Glu Leu Asn Trp Asn Asn
                165             170             175

Arg Phe Leu Asn His Cys Leu Glu His Leu Val Gln Tyr Arg Thr Asp
            180             185             190

Trp Asp His Ser Trp Thr Glu Gln Ser Val Asp Tyr Arg His Lys Phe
        195             200             205

Ser Leu Pro Ser Val Asp Gly Gln Lys Arg Tyr Thr Phe Arg Val Arg
    210             215             220

Ser Arg Phe Asn Pro Leu Cys Gly Ser Ala Gln His Trp Ser Glu Trp
225             230             235             240

Ser His Pro Ile His Trp Gly Ser Asn Thr Ser Lys Glu Asn Pro Phe
            245             250             255

Leu Phe Ala Leu Glu Ala Val Val Ile Ser Val Gly Ser Met Gly Leu
            260             265             270

Ile Ile Ser Leu Leu Cys Val Tyr Phe Trp Leu Glu Arg Thr Met Pro
        275             280             285

Arg Ile Pro Thr Leu Lys Asn Leu Glu Asp Leu Val Thr Glu Tyr His
    290             295             300

Gly Asn Phe Ser Ala Trp Ser Gly Val Ser Lys Gly Leu Ala Glu Ser
305             310             315             320

Leu Gln Pro Asp Tyr Ser Glu Arg Leu Cys Leu Val Ser Glu Ile Pro
            325             330             335

Pro Lys Gly Gly Ala Leu Gly Glu Gly Pro Gly Ala Ser Pro Cys Asn
            340             345             350

Gln His Ser Pro Tyr Trp Ala Pro Pro Cys Tyr Thr Leu Lys Pro Glu
        355             360             365

Thr
```

The present invention applies mutational analysis to determine minimal regions within Jak3 and γ$_c$ that permit such interactions. For example, a point mutation (Y100C) within the Janus homology domain 7 (JH7) of Jak3 prevents kinase-receptor interaction resulting in a loss of IL-2-induced signaling in a B-cell line derived from a patient having this defect.

In still another aspect, the invention demonstrates that a Jak3/Jak1 chimera containing only minimal JH6 and JH7 domains of Jak3 interacts with γ$_c$ and can reconstitute IL-2-dependent responses, including receptor phosphorylation and activation of signal transducer and activator of transcription (STAT) 5b.

The present invention provides various muteins within the Jak3 and γ$_c$ regions that prevent interaction, e.g., one mutein comprises Janus homology domain 7 (JH7) with wild-type flanking sequence. For example, a particular substitution mutations L98A and I102A prevents Jak3 kinase-receptor interaction.

Insight into the function of this region of Jak3 leads to the recognition of which specific Jak3 amino acid residues bind respectively to the IL-2 receptor beta (IL-2Rβ) and common gamma (γ$_c$) chains, thereby initiating biochemical signals critical in controlling immune responses. Additionally, knowledge of Jak3 leads to recognition of a region within Jak3 that has the ability to specifically interact with γ$_c$.

Furthermore, the invention encompasses a Jak3/Jak1 chimeric composition containing which is sufficient to mediate cell inducing responses to various cytokines, e.g., IL-2, IL-4, IL-7, IL-9, IL-13, and IL-15.

Although the N-terminal half of the Jak kinases, containing the JH7-JH3 domains, has been shown to be required for receptor interaction in several systems, the precise nature of the interaction has not been resolved.

Experiments with Jak2/Jak1 chimeras have suggested that the JH7-JH6 domains of Jak2 are sufficient for physical association to IFN-γR2 by co-immunoprecipitation, and IFN-γ-inducible STAT 1 activation in a Jak2-deficient cell line. See, e.g., Kohlhuber, et al. (1997) *Mol. Cell. Biol.* 17:695–706. Reciprocal experiments using Jak1/Jak2 chimeras suggest that the entire amino-terminal half (JH7-JH3) of Jak1 is required for binding to the IFN-γRI and STAT1 activation. See, e.g., Kohlhuber, et al. (1997) *Mol. Cell. Biol.* 17:695–706. Deletion analysis has shown that the N-terminal 239 amino acids (JH7-JH6) of Jak2 are indispensable for granulocyte-macrophage colony stimulating factor (GM-CSF) and growth hormone (GH) receptor association. See, e.g., Frank, et al. (1995) *J. Biol. Chem.* 270, 14776–14785; and Zhao, et al. (1995) *J. Biol. Chem.* 270:13814–13818. In addition, work by Pellegrini and colleagues has demonstrated that the N-terminal half of Tyk2 is required for IFN-$\alpha$ receptor stabilization in a Tyk2-deficient cell line, and for efficient IFN-$\alpha$ induced phosphorylation. See, e.g., Gauzzi, et al. (1997) *Proc. Nat'l Acad. Sci. USA* 94:11839–11844. The relevance of Jak1 and Jak2 structure and function to Jak3 signaling remains uncertain and unpredictable.

In the IL-2 receptor system, a fragment of Jak3 containing JH6 and JH7 could bind $\gamma_c$, but reconstitution of IL-2-induced responses was shown only with a larger region consisting of the JH7-JH4 domains. Thus, although the regions of certain Janus kinases necessary for receptor association are clearly in the amino-terminus, as yet, the shortest regions or discrete domains required, especially in Jak3, has not been defined.

The membrane-proximal region of the cytoplasmic tail of particular cytokine receptors, known as box1/box2 (Murakami, et al. (1991) *Proc. Nat'l Acad. Sci. USA* 88:11349–11353) have been shown to be required for signaling and are thought to interact with Jak kinases. Specifically, mutational analysis of the proline-rich box1 region of gp130 has revealed a major role for this short 8 amino acid motif in the binding of Jak2. See, e.g., Tanner, et al. (1995) *J. Biol. Chem.* 270:6523–6530. Although this box1 region of receptors is loosely conserved, each receptor has a proline-rich motif within box1 and mutations within this region can disrupt certain Jak associations. Interestingly, a point mutation (L271Q) in the box1 region of $\gamma_c$ disrupts Jak3-$\gamma_c$ interaction and causes X-linked combined immunodeficiency. See, e.g., Russell, et al. (1994) *Science* 266:1042–1045; and Schmalstieg, et al. (1995) *J. Clin. Invest.* 95:1169–1173. Therefore, although Jaks interact with box1/box2 in the cytoplasmic domains of hematopoietic receptors, the region of Jaks that interact with box1 has not been fully characterized, much less what region of Jak3 interacts with box1 of $\gamma_c$.

The present invention teaches that a single point mutation in Jak3 (Y100C) can lead to a severe phenotype, similar to that found in an autosomal SCID condition, by blocking Jak3 interaction with its cognate receptor $\gamma_c$ and hence downstream signaling responses to IL-2. Other point mutations in the JH7 region also block binding of Jak3 with $\gamma_c$. This discovery has been used to further define a region within the JH6-JH7 domain of Jak3 that interacts with box1 of the $\gamma_c$ receptor chain. The invention herein also teaches that a Jak3/Jak1 chimera containing the entire JH6-JH7 domain can functionally interact with $\gamma_c$, and can reestablish typical IL-2 signaling. The invention further teaches that the specificity of Jak3 kinase receptor interaction is contained within a defined region of the N-terminus of Jak3 and that the JH6–JH7 domains of Jak3 are necessary for $\gamma_c$ mediated signaling responses.

The present invention provides sequence variants, also referred to as mutant proteins (muteins), of Jak3 and $\gamma_c$ polypeptides and fragments, e.g., muteins, which serve as agonists and/or antagonists of cytokine signaling. The natural cytokine receptor ligands are capable of mediating various biochemical responses which should lead to biological or physiological responses in target cells, e.g., as described above. In particular, the T cell specificity of these cytokines may lead to important regulation of immune responses.

Physically and structurally, many relevant Janus kinase sequences have been previously described, e.g., Leonard and O'Shea (1998) *Annu. Rev. Immunol.* 16:293–322; and Duhe, et al. (1998) *J Interferon Cytokine Res.* 18:1–15. Human Janus kinase 3 (Jak3) sequence is publicly available, e.g., from GenBank (see e.g., Accession Numbers U70065, AC005952, AC005952, AC005759, AC005759, AC005759 and others). Likewise, the sequence of the cytokine receptor gamma common chain $\gamma_c$ is publicly available, e.g., from GenBank (see, e.g., Accession Numbers 400048, 2494714, 729281, and 461904).

A mutein candidate antagonist is tested, preferably with a sequence substitution as described, e.g., by measuring Jak3 interaction with its cognate receptor $\gamma$ common chain. Alternatively, fragments of the two interacting partners may be used. In one assay, a dose response curve of the Jak3 or $\gamma_c$ is titrated in the absence or presence of the candidate mutein at a fixed concentration. Typically, the candidate mutein concentration is fixed, preferably within the range of equimolar to the half-maximum of the target Jak kinase, or at a 10-, 100-, or 1000-fold excess of candidate mutein over that half-maximum amount. Typically, the dose response curve of the Jak kinase will shift. The shift will normally be at least one log unit, often two to four log units.

To test partial agonist activity of the candidate mutein, a dose-response curve of the mutein is performed. Assays for biological activity in vitro or in animals are known. Typically, the maximal stimulatory activity of the mutein will be near that of the natural Jak kinase, but partial agonists will show a suboptimal stimulation at saturation, e.g., the maximal activity will plateau at a lesser amount. This amount will often be less than about 90%, preferably less than about 75%, more preferably less than about 50%, and in most preferred embodiments, even less than about 25%. Agonists with an even lesser maximum will still be useful, and often provide the most promising candidates for establishing chemical antagonist properties.

Super-activating agonists will have greater activities. These activity amounts will often be greater than 110%, typically greater than 120%, preferably greater than 130%, and in most preferred embodiments, greater than 150%, including 2-, 3-, and 5-fold.

Muteins are made typically by site specific mutagenesis at defined positions, but synthetic methods may be applied. As described above, sequences of human Jak3 and $\gamma_c$ proteins are available from GenBank (see Accession Number U70065, and others) and the references cited therein. Initially, single and low multiplicity mutagenesis will be constructed, with more complex combinations possible. Significant changes in the nature of solvent exposed residues, e.g., charge reversal or significant size or hydrophobicity change, would be more likely to significantly affect physiological result. Also, significant disruption of the secondary structure, e.g., helical structure, would be also expected to abolish receptor interaction. Conservative substitutions generally would be expected to exhibit similar biological activity.

II. Agonists; antagonists

The process of inhibition or prevention of signaling responses is termed antagonism, and chemical entities with such properties are antagonists. See, e.g., Kenakin (1987) *Pharmacological Analysis of Drug-Receptor Interaction* Raven Press, NY.

Various classes of antagonists include chemical or neutralization antagonists, competitive antagonists, and noncompetitive antagonists. The chemical or neutralization antagonists typically interact with the interacting partners and prevent continued activation of the signaling pathway and subsequent response, e.g., antibody antagonists which bind to one of the partners and block signaling thereby. Variant proteins are purified and subjected to physical analysis, e.g., CD analysis, to determine whether the protein has a native-like conformation. Its binding behavior is tested, e.g., on cells expressing natural or recombinant Jak3 and $\gamma_c$. The effects of the Jak3 and $\gamma_c$ mutein variants may also be tested in knockout mice, e.g., Jak3$^-$/Jak3$^-$ or $\gamma_c^-$/$\gamma_c^-$ animals.

The competitive antagonists typically are molecules which bind to the same recognition site on Jak3 or $\gamma_c$ and block physiological binding. Noncompetitive antagonists bind to a site on Jak or $\gamma_c$ distinct from the agonist binding site, and block other signal transduction.

Measurement of antagonist activity and analysis of these results can be performed, e.g., by Schild analysis. See Arunlakshana and Schild (1959) *Br. J. of Pharmacol.* 14:48–58; Chapter 9 of Kenakin (1987) *Pharmacological Analysis of Drug-Receptor Interaction* Raven Press, NY.; and Black (1989) *Science* 245:486–493. Schild analysis with a defined antagonist provides a number of means to evaluate quantity and quality of both interacting partner preparations. For example, analysis of a preparation of partners allows better quality control indications than ELISA or mere bioassay quantitation methods. It provides means to distinguish between a denatured partner, which is more likely to test positive in ELISA assays, and a biologically active signaling molecule.

The described muteins are typically proteinaceous, though a full length natural polypeptide is not necessary. Fragments can be useful, e.g., where they include positions which have been mutated as provided herein.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids. Virtually full length molecules with few substitutions will be preferred in most circumstances.

Substantially pure typically means that the mutein is free from other contaminating proteins, nucleic acids, and other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS or CHAPS, or a low enough concentration as to avoid significant disruption of structural or physiological properties of the ligand.

III. Physical Variants

This invention also encompasses proteins or peptides having sequence variations at positions corresponding to the specified residues, but with substantial amino acid sequence identity at other segments. The variants include species variants and particularly molecules with the same primary sequence but variations beyond primary amino acid sequence, e.g., glycosylation or other modifications.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Warps, String Edits, and Macromolecules: The Theory and Practice of Seauence Comparison* Addison-Wesley, Reading, Mass.; and software packages from IntelliGenetics, Mountain View, Calif.; and the University of Wisconsin Genetics Computer Group, Madison, Wis.;. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Members of a group do exhibit less dramatic structural differences, which may also be important. Substitutions at designated positions, e.g., at solvent exposed residues, can often be made with homologous residues to retain similar activities, e.g., agonist or antagonist functions. Identity measures will be at least about 85%, usually at least about 95%, preferably at least about 97%, and more preferably at least 98% or more, especially about the particular residue positions identified as appropriate for sequence changes. Regions of particular importance are within about 5 amino acids surrounding the defined positions, more particularly within about 8 amino acids, and preferably within about 11 amino acids adjacent the positions where changes are indicated.

The isolated kinase DNA can be readily modified by nucleotide substitutions, nucleotide deletions, nucleotide insertions, and inversions of nucleotide stretches. These modifications result in novel DNA sequences which encode these proteins having many similar physiological, immunogenic, antigenic, or other functional activity. Enhanced expression may involve gene amplification, increased transcription, increased translation, and other mechanisms.

Janus kinase mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Meth. Enzymol.* 154:367–382.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

"Derivatives" of these kinases include amino acid sequence mutants at other positions remote from those specified, glycosylation variants, and covalent or aggregate conjugates with other chemical moieties. Covalent derivatives can be prepared by linkage of functionalities to groups which are found in amino acid side chains or at the N- or C-termini, by standard means. See, e.g., Lundblad and Noyes (1988) *Chemical Reagents for Protein Modification*, vols. 1–2, CRC Press, Inc., Boca Raton, Fla.; Hugli (ed. 1989) *Techniques in Protein Chemistry*, Academic Press, San Diego, Calif.; and Wong (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between these kinase muteins and other homologous or heterologous proteins are also provided. Many growth factors and kinases are homodimeric entities, and a repeat construct may have various advantages, including lessened susceptibility to proteolytic cleavage. Typical examples are fusions of a reporter polypeptide, e.g., luciferase, with a segment or domain of a ligand, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds. 1993) *Current Protocols in Molecular Biology*, Greene and Wiley, NY. Techniques for synthesis of polypeptides are described, e.g., in Merrifield (1963) *J. Amer. Chem. Soc.* 85:2149–2156; Merrifield (1986) *Science* 232:341–347; and Atherton, et al. (1989) *Solid Phase Peptide Synthesis: A Practical Approach*, IRL Press, Oxford; and Grant (1992) *Synthetic Peptides: A User's Guide*, W. H. Freeman, NY.

This invention also contemplates the use of derivatives of these Jak3 or γ muteins other than mere variations in amino acid sequence or glycosylation. Such derivatives may involve covalent or aggregative association with chemical moieties. Covalent or aggregative derivatives will be useful as immunogens, as reagents in immunoassays, or in purification methods such as for affinity purification of receptors or other binding ligands. A Jak3 or $\gamma_c$ mutein can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-kinase antibodies or its receptor. The Jak3 or $\gamma_c$ muteins can also be labeled with a detectable group, for use in diagnostic assays. Purification of Jak3 or $\gamma_c$ muteins may be effected by immobilized antibodies or receptor.

The present invention contemplates corresponding muteins the isolation of additional closely related species variants, e.g., rodents, lagomorphs, carnivores, artiodactyla, perissodactyla, and primates.

The invention also provides means to isolate a group of related muteins displaying both distinctness and similarities in structure, expression, and function. Elucidation of many of the physiological effects of the muteins will be greatly accelerated by the isolation and characterization of distinct species variants.

The isolated genes encoding muteins will allow transformation of cells lacking expression of a corresponding Jak3 or $\gamma_c$ protein, e.g., either species types or cells which exhibit negative background activity.

Dissection of critical structural elements which effect the various receptor mediated functions provided by kinase binding is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

IV. Nucleic Acids

The described peptide sequences are readily made by expressing a DNA clone encoding the mutein, e.g., modified from a natural source, or a synthetic gene. The synthetic gene may be based upon a preferred codon usage, e.g., for production in bacteria. A number of different approaches should be available to successfully produce a suitable nucleic acid clone.

The purified protein or defined peptides are useful as described above. Synthetic peptides or purified protein can be presented to an immune system to generate monoclonal or polyclonal antibodies which recognize specifically the muteins. See, e.g., Coligan (1991) *Current Protocols in Immunology* Wiley/Greene; and Harlow and Lane (1989) *Antibodies: A Laboratory Manual*, Cold Spring Harbor Press.

This invention contemplates use of isolated DNA or fragments to encode a biologically active corresponding mutein. In addition, this invention covers isolated or recombinant DNA which encodes a biologically active antagonist or partial agonist protein or polypeptide.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, marker or purification tags, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides. Of particular interest are a plurality of distinct, e.g., nonoverlapping, segments of specified length. Typically, the plurality will be at least two, more usually at least three, and preferably 5, 7, or even more. While the length minima are provided, longer lengths, of various sizes, may be appropriate, e.g., one of length 7, and two of length 12.

Recombinant clones derived from genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502–1504; Travis (1992) *Science* 256:1392–1394; Kuhn, et al. (1991) *Science* 254:707–710; Capecchi (1989) *Science* 244:1288; Robertson (ed. 1987) *Teratocarcinomas and Embryonic Stem Cells: A Practical Approach*, IRL Press, Oxford; and Rosenberg (1992) *J. Clinical Oncology* 10:180–199.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence encoding a mutein. Hybridization under stringent conditions should give a background of at least 2-fold over background, preferably at least 3–5 or more.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needlman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351–360. The method used is similar to the method described by Higgins and Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403–410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

V. Antibodies

Antibodies can be raised to portions of Jak3 or $\gamma_c$ polypeptides and which bind specifically or selectively to the muteins described herein, including species or allelic variants, and fragments thereof. Additionally, antibodies can be raised to Jak3 or $\gamma_c$ muteins in either their active forms or in their inactive forms. Anti-idiotypic antibodies are also contemplated.

Antibodies, including binding fragments and single chain versions, against predetermined fragments of the ligands can be raised by immunization of animals with conjugates of fragments with immunogenic proteins. Monoclonal antibodies are prepared from cells secreting the desired antibody. These antibodies can be screened for binding to fragments containing sequences including the specified modifications. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better.

The antibodies of this invention can also be useful in diagnostic applications. See e.g., Chan (ed. 1987) *Immunology: A Practical Guide*, Academic Press, Orlando, Fla.; Price and Newman (eds. 1991) *Principles and Practice of Immunoassay*, Stockton Press, N.Y.; and Ngo (ed. 1988) *Nonisotopic Immunoassay*, Plenum Press, N.Y.

Mutein fragments may be joined to other materials, particularly polypeptides, as fused or covalently joined polypeptides to be used as immunogens. A mutein or its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; Williams, et al. (1967) *Methods in Immunology and Immunochemistry*, vol. 1, Academic Press, New York; and Harlow and Lane (1988) *Antibodies: A Laboratory Manual*, CSH Press, NY, for descriptions of methods of preparing polyclonal antisera. Alternatively, muteins may be attached to other solid substrates, e.g., to immobilize or as a synthetic substrate for synthesis.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.), Academic Press, New York; and particularly in Kohler and Milstein (1975) in *Nature* 256:495–497, which discusses one method of generating monoclonal antibodies. Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029–10033.

The antibodies of this invention can also be used for affinity chromatography in isolating the Jak3 or $\gamma_c$ proteins or polypeptides. Columns can be prepared where the antibodies are linked to a solid support. See, e.g., Wilchek, et al. (1984) *Meth. Enzymol.* 104:3–55.

Antibodies raised against each mutein will also be useful to raise anti-idiotypic antibodies. These will be useful in detecting or diagnosing various immunological conditions related to expression of the respective antigens.

VI. Making Agonists and Antagonists

DNA which encodes the Jak3 or $\gamma_c$ proteins or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161–170; Gubler and Hoffman (1983) *Gene* 25:263–269; and Glover (ed. 1984) *DNA Cloning: A Practical Approach*, IRL Press, Oxford. Suitable sequences can be obtained from GenBank. Biological mutagenesis methods of libraries may be applied to prepare variant polypeptides.

This DNA can be mutated for expression in a wide variety of host cells for the synthesis of mutein or fragments which can in turn, e.g., be used to generate polyclonal or monoclonal antibodies; for binding or screening studies; for construction and expression of modified molecules; and for structure/function studies. Combinatorial methods may be applied to prepare variants.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual*, Elsevier, N.Y.; and Rodriguez, et al. (eds. 1988) *Vectors: A Survey of Molecular Cloning Vectors and Their Uses*, Buttersworth, Boston, Mass.

For purposes of this invention, DNA sequences are operably linked when they are functionally linked to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See e.g., Rodriguez, et al., Chapter 10, pp. 205–236; Balbas and Bolivar (1990) *Methods in Enzymology* 185:14–37; and Ausubel, et al. (1993) *Current Protocols in Molecular Biology*, Greene and Wiley, NY.

Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610, see, e.g., Miller (1988) *Ann. Rev. Microbiol.* 42:177–199.

It will often be desired to express a mutein or polypeptide in a system which provides a specific or defined glycosylation pattern. See, e.g., Luckow and Summers (1988) *Bio/Technology* 6:47–55; and Kaufman (1990) *Meth. Enzymol.* 185:487–511.

The appropriate mutein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Once a particular mutein has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; Villafranca (ed. 1991) *Techniques in Protein Chemistry II*, Academic Press, San Diego, Calif.; and Coligan, et al. (eds. 1996 and periodic supplements) Current Protocols in Protein Science John Wiley and Sons, Inc., New York, N.Y. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes. See also chemical ligation, e.g., Dawson, et al. (1994) *Science* 266:776–779, a method of linking long synthetic peptides by a peptide bond.

VII. Uses

The present invention provides reagents which will find use in therapeutic or diagnostic applications as described elsewhere herein, e.g., in the general description for developmental abnormalities, or below in the description of kits for diagnosis.

The Jak3 or $\gamma_c$ polypeptides, muteins, fragments thereof, and antibodies thereto, should be useful in the evaluation or quality control of Jak3 or $\gamma_c$ constructs or fragments. They may also be useful in vitro or in vivo screening or treatment of conditions associated with abnormal physiology or development, including abnormal proliferation, e.g., cancerous conditions, or degenerative conditions and severe infections due to reduced levels of T and natural killer (NK) cells, as well as hypogammaglobulinemia. The structural relationship of the Jak3 or $\gamma_c$ protein to other Jak kinases suggests the possibility of biological activities beyond the Severe Combined Immunodeficiencies described patients with specific mutations in either the $\gamma_c$ subunit of a cytokine receptor (e.g., IL-2, IL-4, IL-7, IL-9, and IL-15) or in the Janus kinase. In particular, modulation of Jak kinase activities should be useful in situations where the Jak kinase functions have been implicated, e.g., lymphoid cell development, immunological responses, inflammation, graft rejection, rheumatoid arthritis, autoimmunity, abnormal proliferation, regeneration, degeneration, and atrophy of responsive cell types. For example, a disease or disorder associated with abnormal expression or abnormal signaling by Jak3 or $\gamma_c$ protein (e.g., SCID, XSCID, inhibition of T cell proliferation, or similar phenotypes, including those described in Candotti, et al. (1998) *Springer Semin. Immunopathol.* 19:401–415; Macchi, et al. (1995) *Nature* 377:65–68; Russell (1994) *Science*: 270:797–799; Morelon, et al. (1996) *Blood* 88:1708–1717; or Schmalstieg, et al. (1995) *J. Clin. Invest.* 95:1169–1173; also in developmental defects of lymphoid development as described in Park, et al. (1995) *Immunity* 3:771–782; Thomis, et al. (1995) *Science* 270:794–797; Macchi, et al., (1995) *Nature* 377:65–68; and Nosaka, et al. (1995) *Science* 270:800–802) besides the recognized effects, should be a potential target for treatment using an antagonist or agonist. The similarity in structures and mechanisms suggest potential hematopoietic or immunological functions may also exist.

Recombinant or synthetic Jak3 or $\gamma_c$ polypeptide muteins or, in some instances, antibodies can be purified and then administered to a patient. These reagents can be combined for therapeutic use with additional active or inert ingredients, e.g., in conventional pharmaceutically acceptable carriers or diluents, e.g., $\gamma_c$ variants, STAT5b, along with physiologically innocuous stabilizers and excipients. They may be combined with other antagonists, e.g., other cytokine antagonists, antibodies, mutein ligands, etc. These combinations can be sterile filtered and placed into dosage forms as by lyophilization in dosage vials or storage in stabilized aqueous preparations. This invention also contemplates use of antibodies or binding fragments thereof, including forms which are not complement binding.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described for the actual dosage of reagent, formulation or composition that modulates a disorder as described herein since the dosage depends on many factors, including the size and health of an organism, however one of one of ordinary skill in the art can use the following teachings describing the methods and techniques for determining clinical dosages. See Spilker (1984) *Guide to Clinical Studies and Develoting Protocols* Raven Press Books, Ltd., New York, pp. 7–13, 54–60; Spilker (1991) *Guide to Clinical Trials* Raven Press, Ltd., New York, pp. 93–101; Craig and Stitzel (eds. 1986) *Modern Pharmacology,* 2d ed., Little, Brown and Co., Boston, pp. 127–133; Speight (ed. 1987) *Avery's Drug Treatment: Principles and Practice of Clinical Pharmacology and Therapeutics,* 3d ed., Williams and Wilkins, Baltimore, pp. 50–56; Tallarida, et al. (1988) *Principles in General Pharmacology,* Springer-Verlag, New York, pp. 18–20; Gilman, et al. (eds. 1990) *Goodman and Gilman's: The Pharmacological Bases of Therapeutics,* 8th ed., Pergamon Press; and *Remington's Pharmaceutical Sciences,* cur. ed., Mack Publishing Co., Easton, Penn. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration. See, e.g., Langer (1990) *Science* 249:1527–533.

The Jak3 or $\gamma_c$ muteins may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) *Goodman and Gilman's: The Pharmacological Bases of Therapeutics,* latest Ed., Pergamon Press; and *Remington's Pharmaceutical Sciences,* latest ed., Mack Publishing Co., Easton, Pa.; Avis, et al. (eds. 1993) *Pharmaceutical Dosage Forms: Parenteral Medications,* Dekker, N.Y.; Lieberman, et al. (eds. 1990) *Pharmaceutical Dosage Forms: Tablets,* Dekker, N.Y.; and Lieberman, et al. (eds. 1990) *Pharmaceutical Dosage Forms: Disperse Systems,* Dekker, N.Y. The therapy of this invention may be combined with or used in association with other agents.

The muteins of this invention are particularly useful in kits and assay methods which are capable of screening compounds for interactions with binding proteins. Interaction of Jak3 JH7/JH6 fragments, e.g., attached to a solid phase, with, e.g., $\gamma_c$ box1/box2 fragments, can be used as the basis for a screening assay. Synthetic or recombinant fragments can be made, and labeled. In, e.g., a 96 well microtiter format, the interaction of the partners can be determined in the presence of candidate blocking compounds or mutein fragments. The partners have sequences disclosed in SEQ ID NO: 1 and 2. Segments of the JH7/JH6 and box1/box2 regions have been defined. See, e.g., Frank, et al. (1995) *J. Biol. Chem.* 270,14776–14785; and Zhao, et al. (1995) *J. Biol. Chem.* 270:13814–13818; and Murakami, et al. (1991) *Proc. Nat'l Acad. Sci. USA* 88:11349–11353. The JH7/JH6 fragments are in the region roughly of 1–256, but defined functionally by those segments which are critical for interaction with the $\gamma_c$ box1/box2 fragments, which run roughly from about 263–315. Conversely, the box1/box2 fragments are roughly in the region of 263–315, and are the essential minimal segments for functional interaction with the JH7/JH6 segment of Jak3. However, further analysis, by the methods described herein, will more narrowly define the respective interacting segments.

Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate.

For example, antagonists can normally be found once the partners have been structurally identified. Testing of potential antagonist compound libraries, including combinatorial chemistry libraries, is now possible, based upon an in vitro or in vivo assay, or upon binding protein interaction. In particular, new agonists and antagonists will be discovered by using screening techniques described herein.

One method of drug screening utilizes eukaryotic or prokaryotic host cells which are stably transformed with recombinant DNA molecules expressing the binding pair. Cells may be isolated which express a binding protein in isolation from any others. Such cells, either in viable or fixed form, can be used for standard binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses.

Rational drug design may also be based upon structural studies of the molecular shapes of the agonists or antagonists and other effectors or analogs. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, *Academic Press, New York*. Drug screening using muteins or fragments thereof or chemical compound libraries can identify compounds having ability to interfere with partner interaction. Alternatively, compounds which block interaction of the Jak3 with $\gamma_c$, e.g., Jak3 JH7/JH6 or $\gamma_c$ box1/box2 muteins, may be identified by screening. Two hybrid type interaction (see, e.g., Fields and Song (1989) *Nature* 340:245–246) can serve as the basis for screening a library of muteins for interfering capability. Subsequent biological assays can then be utilized to determine if the compound has intrinsic interfering activity and is therefore an antagonist in that it blocks the signal process.

VIII. Kits

This invention also contemplates use of the muteins of the invention, proteins, polypeptides, fragments thereof, and their fusion products in a variety of diagnostic kits and methods for diagnosing or screening for antagonists of the binding interactions of a Jak3 kinase with a $\gamma_c$ polypeptide. Typically the kit will have a means of sequestering either a defined mutein peptide (e.g., compartment, affixed to a substrate etc.) or a means of sequestering a partner or reagent which recognizes one, e.g., Jak3 or $\gamma_c$ receptor fragments or antibodies.

A kit for determining the binding affinity of a test compound to a binding protein or receptor would typically comprise a test compound; a labeled compound, for example a receptor or antibody having known binding affinity for the Jak kinase or its mutein; a source of mutein; and a means for separating bound from free labeled compound, such as a solid phase for immobilizing the mutein. Once compounds are screened, those having suitable binding affinity can be evaluated in suitable biological assays, as are well known in the art, to determine whether they act as antagonists.

Antibodies, including antigen binding fragments, specific for muteins or unique fragments are useful in diagnostic applications to detect the presence of the muteins. In certain circumstances, it will be useful to quantitate amounts of muteins in a sample. Diagnostic assays may be homogeneous (without a separation step between free reagent and antigen-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol*. 70:1–525; Harlow and Lane (1980) *Antibodies: A Laboratory Manual*, CSH Press, NY.; and Coligan, et al. (eds. 1993) *Current Protocols in Immunology*, Greene and Wiley, NY.

Anti-idiotypic antibodies may have similar use to diagnose presence of antibodies against a mutein, as such may be diagnostic of various abnormal states.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled mutein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In many of these assays, the test compound, mutein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free partner, or alternatively the bound from the free test compound. A mutein can be immobilized on various matrixes followed by washing. Suitable matrixes include plastic such as an ELISA plate, filters, and beads. See, e.g., Coligan, et al. (eds. 1993) *Current Protocols in Immunology*, Vol. 1, Chapter 2, Greene and Wiley, NY. Other suitable separation techniques include, without limitation, the fluorescein antibody magnetizable particle method described in Rattle, et al. (1984) *Clin. Chem*. 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res*. 1:89–97.

All references cited herein are incorporated herein by reference to the same extent as if each individual publication or patent application was specifically and individually indicated to be incorporated by reference.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual* (2d ed.), vols. 1–3, CSH Press, NY; Ausubel, et al., *Biology*, Greene Publishing Associates, Brooklyn, N.Y.; Ausubel, et al. (1987 and Supplements) *Current Protocols in Molecular Biology*, Greene and Wiley, New York; Innis, et al. (eds. 1990) *PCR Protocols: A Guide to Methods and Applications*, Academic Press, NY; or Coligan, et al. (eds. 1996 and periodic supplements) *Current Protocols in Protein Science* John Wiley and Sons, Inc., New York, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; Crowe, et al. (1992) *OIAexpress: The High Level Expression & Protein Purification System* QIAGEN, Inc., Chatsworth, Calif.; and Coligan, et al. (eds. 1996 and periodic supplements) Current Protocols in Protein Science John Wiley and Sons, Inc., New York, N.Y. Cell culture techniques are described in Doyle, et al. (eds. 1994) *Cell and Tissue Culture: Laboratory Procedures*, John Wiley and Sons, NY.

This application incorporates by reference U.S. Provisional Patent Application U.S. Ser. No. 60/008,574 by Altmann, et al. filed Dec. 6, 1995, which generally describes various mutational variants directed to cytokines.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

Cell lines and cytokines.

15 293T cells (DuBridge, et al. (1987) *Mol. Cell. Biol.* 7:379–387) IL-2R-expressing fibroblasts 3T3αβγ (Chen, et al. (1997) *Proc. Nat'l Acad. Sci. USA* 94:6910–6915) and Phoenix A cells (Grignani, et al. (1998) *Cancer Res.* 58:14–19) were maintained in DMEM (Biowhittaker, Walkersville, Md.) and cultured at 37° C. in 5% $CO_2$, and were transfected by the calcium phosphate method. All tissue culture media were supplemented with 10% fetal bovine serum (FBS; Hyclone, Logan, Utah), 2 mM L-glutamine, 100 U/ml penicillin, and 100 µg/ml streptomycin (Bio-Whittaker, Walkersville, Md.). The EBV-transformed B-cell lines GM, JY, and MC were maintained in RPMI 1640 (Bio-Whittaker, Walkersville, Md.). Interleukin-2 was purchased from R&D Systems (Minneapolis, Minn.).

Plasmids and constructs.

Jak3 or $\gamma_c$ point mutations were generated by standard PCR techniques, using oligonucleotides encoding the mutant sequence. Methods for expression of a mutein, e.g., a Jak3 variant protein, are described in, e.g., Coligan, et al. (eds. 1996 and periodic supplements) *Current Protocols in Protein Science* John Wiley and Sons, Inc., New York, N.Y. Cassette substitution mutagenesis is demonstrated in Zurawski and Zurawski (1989) *EMBO J.* 8:2583–2590. For instance, a synthetic gene may be constructed by linking synthetic oligonucleotides, the gene sequence selected from preferred codon usage in, e.g., *E. coli*. In addition, a purification sequence, e.g., a FLAG signal may be added to assist in purification and/or detection. Refolding of recombinant protein may be performed using standard methods. Jak3, Jak3 mutants, and $\gamma_c$ were FLAG or MYC tagged at their carboxy-termini by PCR. The stop codon of each cDNA was replaced, e.g., by a ClaI site (ATCGAT), and the cDNA was cloned into pME18S, in which expression is driven by the SR α promoter (Takebe, et al. (1988) *Mol.*

*Cell. Biol.* 8:466–472), and the pMX Neo retroviral vector (Onishi, et al. (1996) *Exp. Hematol.* 24:324–329), which contains either a single copy of the FLAG sequence or a pentamer of the Myc-tag sequence. Jak3/Jak1 chimeras were generated, e.g., by fusion PCR (Clackson and Winter (1989) *Nucl. Acids Res.* 17:10163–10170) with the following junctions (amino acid position): J3 109/J1 105, J3 130/J1140, J3 193/J1 209, J3 256/J1 278, J3 300/J1 326, J3 519/J1 570. The Jak3/Jak1 chimeras were FLAG-tagged at their carboxy-termini by PCR, in which the 3' oligonucleotide encoded the FLAG sequence. Jak3 fragments were generated by PCR, introducing a ClaI site after the coding sequence, and were cloned into pME18S encoding the carboxy-terminal Myc tag.

Cytokine Stimulation, Immunoblotting, and Immunoprecipitation.

For the 293T coimmunoprecipitation experiments, cells were lysed in buffer containing 300 mM NaCl, 50 mM Tris-HCl, 2 mM EDTA, 0.875% Brij 97 (Sigma, St. Louis, Mo.), 0.125% NP40, 10 µg/ml aprotinin, 10 µg/ml leupeptin, 1 mM PMSF, 1 mM $Na_3VO_4$, and 1 mM NaF. Lysates were centrifuged at 12,000×g, and NaCl was added to 500 mM final concentration. Lysates were immunoprecipitated with the appropriate antibody. Rabbit polyclonal, mouse monoclonal (M2), and Sepharose-conjugated M2 anti-FLAG antibodies were purchased from Kodak Scientific Imaging Systems (Rochester, N.Y.), Goat anti-$\gamma_c$ antibody was purchased from R&D (Minneapolis, Minn.). Lysates were boiled, and subjected to 8% SDS-PAGE or 12% SDS-PAGE for experiments with Jak3 fragments, and electrotransferred onto nylon membranes (Immobilon-P, Millipore, Bradford, Mass.). Membranes were probed with one of the following antibodies: Mouse monoclonal M2 anti-FLAG antibody, rabbit polyclonal anti-$\gamma_c$ antibody, or mouse monoclonal anti-Myc tag antibody 9E10 (Santa Cruz Biotechnology, Santa Cruz, Calif.). For the immunoprecipitation with EBV-transformed B cell lines and the IL-2R expressing fibroblasts, cells were lysed as described above, except with a final NaCl concentration of 150 mM. Lysates were immunoprecipitated with monoclonal (M2) anti-FLAG antibody, rabbit polyclonal antibody directed against the C-terminus of Jak3 (α-Jak3; Kawamura, et al. (1994) *Proc Nat'l Acad Sci USA* 91:6374–8) or rabbit polyclonal antibody specific for STAT5b (Santa Cruz Biotechnology, Santa Cruz, Calif.). Immunoprecipitates were then washed, boiled, and resolved using SDS-PAGE. Precipitated complexes were immunoblotted with anti-phosphotyrosine mouse monoclonal antibody (α-PY [4G10]; Upstate Biotechnology Inc., Lake Placid, N.Y.), or reprobed with the original immunoprecipitation antibody as described (Johnston, et al. (1994) *Nature* 370:151–153).

Detection was then performed by enhanced chemiluminescence (ECL, Pierce, Rockport, Ill.).

Retroviral infections and stable cell lines.

IL-2R-expressing fibroblasts were infected with supernatant from the Phoenix A packaging cell line that had been transfected with Wild-type Jak3, mutant Jak3, Jak3/Jak1 chimera or STAT 5b cDNA's cloned onto the retroviral expression vector pMX-Neo. Onishi, et al., (1996) *Exp. Hematol.* 24: 324–329. Stably expressing cell lines were selected in 0.5 mg/ml G418 (Gibco BRL, Gaithersburg, Md.).

II: Jak3 mutation (Y100C) blocks IL-2-induced tyrosine phosphorylation.

Severe Combined Immunodeficiency (SCID) can result from several distinct molecular defects. See, e.g., Candotti and Blaese (1998) *Springer Semin. Immunopathol.*

19:401–415. The X-linked form of the disease results from loss or mutation of $\gamma_c$, and a clinical phenotype indistinguishable from autosomal SCID, which is due to loss or mutation of Jak3, and results in impaired signaling through $\gamma_c$-using cytokine receptors. While some cases of autosomal SCID result from the absence of Jak3 protein, several patients have been identified who express detectable levels of Jak3.

An EBV-transformed B-cell line from an autosomal SCID patient (GM) expressed Jak3 levels comparable to an EBV-transformed normal cell line expressing wild-type (WT) Jak3. The SCID patient (GM) has a single amino acid substitution, Y100C, in the JH7 domain of Jak3.

Therefore, to discover whether this SCID patient's Y100C mutation affects Jak3 signaling ability, an EBV-transformed B-cell line derived from GM was tested for IL-2 induced phosphorylation of Jak3.

The SCID patient cell line (GM) and a control cell line from a patient expressing WT endogenous Jak3 were incubated in serum-free medium for 4 h prior to challenge with IL-2 (1000 U/ml IL-2 for 15 min at 37° C.).

Lysates from normal control, a Jak3-negative SCID patient (JY), a Jak3-expressing SCID patient (GM), and a positive control human T cell line, KIT 225, were subjected to SDS-PAGE and electro-transferred to a nylon membrane. The filter was immunoblotted with Jak3 antiserum ($\alpha$-Jak3), stripped and then reblotted with Jak1 antiserum (($\alpha$-Jak1) to verify equal loading. Lysed cells and lysates were immunoprecipitated with rabbit polyclonal antibody specific for the C-terminus of Jak3. The blot was probed with anti-Phosphotyrosine ($\alpha$-PY antibody 4G10.

The results demonstrated that Jak3 was tyrosine phosphorylated in response to IL-2 stimulation in normal EBV B-cells. However, cells of the SCID patient (GM), demonstrated no detectable tyrosine phosphorylation of Jak3 in response to IL-2, although Jak3 Y100C was constitutively tyrosine phosphorylated in the absence of cytokine treatment. The expression controls showed that the levels of precipitated endogenous Y100C were lower compared to WT Jak3, demonstrating that the Jak3 Y100C phosphorylation state in the absence of IL-2 does not result from Jak3 Y100C overexpression.

Downstream signaling in the GM patient cell line was further analyzed by examining the phosphorylation of the transcription factor STAT5b. Again, EBV-transformed B cell lines were incubated in serum-free medium for 4 h prior to IL-2 stimulation for 15 min as described above. Lysates were then immunoprecipitated with rabbit polyclonal anti-STAT5b antibody and the resulting blot was probed with anti-phosphotyrosine antibody 4G10.

The results demonstrated that STAT5b became tyrosine phosphorylated in response to IL-2 stimulation in the Jak3-negative SCID patient (JY) cells, but not in response to IL-2 stimulation in the Jak3-expressing SCID patient (GM) cells. The lack of IL-2-induced responses in the SCID patient GM was not due to loss or downregulation of IL-2 receptor components, as the levels of the IL-2 receptor components IL-2R$\beta$ and $\gamma_c$ were equal in both the GM and JY cell lines. These results suggest that although Y100C Jak3 was constitutively phosphorylated in both the GM and JY cells, Y100C Jak3 was not inducibly phosphorylated and was unable to initiate downstream signaling events in response to IL-2 stimulation.

III. Jak3 Y100C mutant fails to interact with $\gamma_c$.

To study the effect of Jak3 mutations on $\gamma_c$ interaction, wild-type (WT) Jak3, two kinase-inactive forms of Jak3, a form of Jak3 with a Y105F mutation in a conserved tyrosine adjacent to Y100, and a Y100C mutant, were expressed in 293T cells, and tested for their ability to co-immunoprecipitate with $\gamma_c$.

Lysates from 293T cells transfected with plasmids encoding FLAG-tagged WT, kinase-inactive mutant Jak3 K855A and Y841F, Y100C, Y105F, and Y100C/Y105F double mutant with $\gamma_c$ were immunoprecipitated with monoclonal anti-FLAG tag antibody M2. Blots were probed with a rabbit polyclonal antibody specific for $\gamma_c$ WT or mutant Jak3.

The results demonstrated that $\gamma_c$ co-immunoprecipitated with WT Jak3, both kinase inactive mutants, K855A and Y841F, and the Y105 mutant. However, co-precipitation of $\gamma_c$ with Jak3 Y100C or the Jak3 Y100C/Y105F double mutant was not observed, although equal levels of Jak3 and $\gamma_c$ were expressed in these cells, suggesting that the Y100C mutation disrupts receptor interaction. The same result was obtained when epitope-tagged $\gamma_c$ was co-precipitated with WT or mutant Jak3. Again, WT, kinase-inactive, and Y105F Jak3 interacted strongly with $\gamma_c$, while the Y100C mutant and the Y100C/Y105F double mutant were unable to bind the receptor, suggesting that Jak3 Y100C lacks the ability to interact with $\gamma_c$.

A naturally occurring point mutation in the cytoplasmic domain of $\gamma_c$ has been reported to impair but not abolish interaction with Jak3. This mutation results in a mild X-linked combined immunodeficiency (XCID). See, e.g., Schmalstieg, et al. (1995) *J. Clin. Invest.* 95:1169–1173. The results presented herein clearly suggest that a Jak3 point mutation in Y100C also disrupts receptor association.

Following IL-2 stimulation, Jak3 rapidly becomes tyrosine phosphorylated and recruited to the receptor complex. See, e.g., Leonard and O'Shea, (1998) *Annu. Rev. Immunol.* 16:293–322. Therefore, the ability of Jak3 Y100C to become tyrosine phosphorylated and recruited to the receptor in response to IL-2 was also investigated.

Fibroblasts that stably express the IL-2 receptor chains (3T3$\alpha\beta\gamma$), see, e.g., Chen, et al. (1997) *Proc. Nat'l Acad. Sci. USA* 94:6910–6915, were infected with retrovirus expressing epitope-tagged WT Jak3, kinase-inactive forms of Jak3, or the Y100C mutant. The IL-2R+ fibroblasts lacking Jak3 or stably expressing FLAG-tagged WT Jak3, kinase-inactive Jak3 K855A or Y841F, or Jak3 Y100C were then stimulated for 15 min with 1000 U/ml IL-2. Next, cells were lysed and lysates were immunoprecipitated with monoclonal anti-FLAG antibody M2 as described above. Blots were first probed with anti-phosphotyrosine monoclonal antibody 4G10 then subsequently stripped and reprobed with rabbit polyclonal antibody specific for $\gamma_c$.

The results demonstrated that a parental cell line, expressing all IL-2 receptor components and Jak1 but lacking Jak3, failed to exhibit tyrosine phosphorylation following IL-2 stimulation. In contrast, in cells expressing WT Jak3 following IL-2 stimulation, Jak3 was rapidly tyrosine phosphorylated and associated with the IL-2 receptor complex. Tyrosine phosphorylation of both kinase-inactive Jak3 proteins, presumably via transphosphorylation by receptor-associated Jak1, was also observed. Although the levels of tyrosine phosphorylation were much reduced compared to wild-type. However, no IL-2-induced phosphorylation of Jak3 Y100C was observed, although we did detect high basal tyrosine phosphorylation, in agreement with our results with the GM patient's cells. The expression controls again showed that the high basal phosphorylation state of Y100C was not due to overexpression of the mutant Jak3, as Y100C was expressed at levels comparable to WT Jak3.

It has been previously shown that unlike other receptor systems, where Jak kinase-receptor association is constitutive, Jak3 is recruited to $\gamma_c$ in response to cytokine. In cells expressing WT Jak3, or kinase inactive Jak3, $\gamma_c$ co-precipitated with Jak3, and an enhanced interaction was observed after IL-2 stimulation. Interestingly, this IL-2-induced association was observed with both WT and kinase-inactive Jak3, suggesting that Jak3 kinase activity was not necessary. However, the cytokine-induced recruitment of Jak3 to the receptor complex was not observed with Jak3 Y100C. These data confirm that the Y100C mutation results in defective interaction with $\gamma_c$.

IV. Other Jak3 mutations that fail to interact with $\gamma_c$.

As the Y100C mutation clearly blocks Jak3-receptor association, other mutations in this region of Jak3 were investigated to determine whether they could also disrupt receptor interaction.

Both WT Jak3 and a kinase-inactive mutant Jak3 interacted strongly with $\gamma_c$. A kinase-inactive form of the patient mutant, Jak3 Y100C/K855A, also did not interact with $\gamma_c$, and anti-phosphotyrosine western blotting confirmed that J3 Y100C/K855A was not phosphorylated in 293T cells, suggesting that the defect in receptor binding is not due to increased or aberrant phosphorylation of the mutant kinase, and that neither kinase activity, nor phosphorylation of Y100 is necessary for $\gamma_c$ interaction. In addition, a Jak3 Y100A mutant fails to bind $\gamma_c$ while a conservative Jak3 Y100F mutant still interacted with $\gamma_c$, presumably by preserving secondary structure required for receptor binding.

Because the Janus homology domains JH6 and JH7 of Jak kinases contains several highly conserved residues, amino acid mutations in this area were created to determine if the region represented a domain that mediates binding to receptor chains. Furthermore, several aliphatic amino acids within this region of Jak3 (e.g., L98, L99, and I102) have been shown to be highly conserved among mammalian Jak kinases. Similar leucine-rich domains in transcription factors, mediate protein-protein interactions and their mutation has been shown to prevent these protein-protein associations. See, e.g., Heery, et al. (1997) *Nature* 387:733–736.

Accordingly, mutations were generated in the highly conserved aromatic amino acids Y105A and W109A of Jak3, however, the mutations had no significant effect on $\gamma_c$ binding in 293T co-immunoprecipitation experiments. In contrast, a triple mutant (L98A, L99A, I102A), effected a marked reduction in $\gamma_c$-Jak3 association as tested by coimmunoprecipitation.

Single amino acid substitutions within this conserved region also affected the $\gamma_c$-Jak3 interaction. Leucine 98A and I102A mutations disrupted the binding of Jak3 to $\gamma_c$ by co-immunoprecipitation, but the L99A mutation had no significant effect, suggesting that very subtle changes in the JH6/JH7 region affect the ability of Jak3 to interact with its cognate receptor.

The combined results demonstrate that a single point mutation in Jak3 (Y100C) produces a severe cellular phenotype by blocking Jak3 interaction with $\gamma_c$ and hence downstream signaling responses to IL-2 stimulation. Other mutations in this region of Jak3 (Y100A, L98A, I102A) also block Jak3-$\gamma_c$ interactions suggesting that this region of Jak3 encodes an amino acid domain that is essential for receptor interaction. Further, the Y100A mutation, like Y100C, dramatically reduces Jak3 receptor binding, while a conservative mutation (Y100F) has no significant effect on Jak3-$\gamma_c$ interaction, strongly supporting the idea that tyrosine 100 of Jak3 is situated in a region that directly contacts $\gamma_c$, therefore, tyrosine 100 mutants disrupt the secondary structure of Jak3 resulting in a reduction in its interaction with $\gamma_c$.

V. Defining a minimal receptor interaction domain on Jak3.

These results suggested that besides containing the Y100C mutation, the JH6/JH7 region of the amino-terminus of Jak3 might also contain a receptor interaction domain. To test this idea, Jak3/Jak1 chimeras and truncations of Jak3 were made. These constructs were transfected into both 293T cells and IL-2R-expressing fibroblasts to test their ability to interact with $\gamma_c$.

The N-terminal JH6/JH7 region of Jak3 encodes 256 amino acids. To test whether partial fragments of this domain were sufficient to interact with $\gamma_c$, a panel of staggered deletion mutants was generated. J3 1–193 encodes all of the JH7 domain and 73 amino acids of the JH6 domain, J3 1–130 encodes all of the JH7 domain and 5 residues of the JH6 domain, J3 1–109 deletes 11 amino acids of the JH7 domain, and J3 72–130 encodes 38 amino acids of the JH7 domain and 5 amino acids of JH6.

Epitope-tagged fragments of Jak3 were co-expressed in 293T cells with $\gamma_c$. Lysates from 293T cells coexpressing $\gamma_c$ and the indicated Jak3/Jak1 chimeras were immunoprecipitated with Sepharose-conjugated M2 anti-FLAG monoclonal antibody, and blots were probed with rabbit polyclonal anti-$g_c$ antibody. The receptor was immunoprecipitated, and blots were probed with antibody recognizing the epitope tagged Jak3 fragments.

The results demonstrate that the shortest region of Jak3 sufficient to interact with $\gamma_c$ was amino acids 72–130. In addition, longer fragments, containing amino acids 1–130 and 1–193 also interacted strongly with $\gamma_c$. However, a region of Jak3 further truncated from the C-terminus, containing amino acids 1–109 is unable to bind $\gamma_c$ in this experiment, suggesting that the $\gamma_c$ binding region of Jak3 can be mapped to a 58 amino acid region consisting of portions of JH6 and JH7.

A number of reports have suggested that the N-termini of Jak kinases are required for receptor interaction. Several studies have shown that deletion of the JH6/JH7 domains of Jak2 abrogates its association with the growth hormone receptor and GM-CSF receptor chain $\beta_c$. See, e.g., Tanner, et al. (1995) *J. Biol. Chem.* 270:6523–6530; Frank, et al. (1995) *J. Biol. Chem.* 270:14776–14785; and Zhao, et al. (1995) *J. Biol. Chem.* 270:13814–13818. This region has also been shown to be required for Tyk2 interaction with IFNαR1. Gauzzi, et al. (1997) *Proc. Nat'l Acad. Sci. USA* 94:11839–11844. The JH7 and JH6 domains were shown to be sufficient for the interaction of Jak2 with GM-CSF $\beta_c$ (Zhao, et al. (1995) *J. Biol. Chem.* 270:13814–13818), and for Jak3 with $\gamma_c$. However, the Janus homology domains are defined based on overall homology between family members and may not represent discrete functional domains, such as SH2 and SH3 domains. The finding that an aminoterminal fragment encoding amino acids 72–130 of Jak3 binds $\gamma_c$ suggests that a region sufficient for receptor interaction does not require the entire JH6 and JH7 domains of Jak3.

VI. Mutations in $\gamma_c$ reduce Jak3 association.

Mutational analysis of cytokine receptors has shown that the cytoplasmic membrane-proximal regions containing box1 (proline-rich motif) and box2 are essential for receptor function and Jak association. For example, deletion or mutation of box1 proline residues abrogates the interaction of Jak2 with several receptor chains, including gp130, GHR, EPOR, and GM-CSF βc. Tanner, et al.(1995) *J. Biol. Chem.* 270:6523–6530.; Zhao, et al. (1995) *J. Biol. Chem.* 270:13814–13818. Similarly, mutational analysis has shown that the box1 region of $\gamma_c$ is necessary for its interaction with Jak3, and deletion of box1 abrogates Jak3-dependent proliferative signals (Nelson, et al. (1996) *Mol. Cell. Biol.*, 16:309–317; Goldsmith, et al. (1995) *J. Biol. Chem.*, 270:21729–21737). Moreover, a patient point mutation adjacent to box1 in γc reduces Jak3 binding and results in X-linked combined immunodeficiency (Schmalstieg, et al. (1995) *J. Clin. Invest.* 95:1169–1173; Russell, et al. (1994) *Science* 266:1042–1045), suggesting that $\gamma_c$ box1 directly contacts Jak3. However, it has not been demonstrated that the conserved proline residues of $\gamma_c$ box1 participate in Jak3 binding.

The membrane-proximal region of the cytoplasmic tail of hematopoietic receptors, specifically, the proline-rich box1 motif, has been implicated as an important point of contact with Jak kinases. A naturally occurring mutation of $\gamma_c$ L271Q from a patient with X-linked combined immunodeficiency (XCID) decreases the association of $\gamma_c$ with Jak3. This single amino acid substitution occurs within the box1 region, just C-terminal to proline-rich sequences in $\gamma_c$ (RTMPRIP) from amino acids 263–269. See, e.g., Puck (1996) *Immunol. Today* 17:507–511.

To determine if the $\gamma_c$ membrane-proximal cytoplasmic tail was also an important contact point for Jak kinase, mutations were created in the proline-rich box1 area of $\gamma_c$ (P266, 269A or P266, 269G). These proline residue mutants were subsequently introduced into 293T cells, and tested for their ability to interact with Jak3.

The 293T cells were cotransfected with WT or mutant Jak3 and WT or mutant $\gamma_c$ in the following combinations: WTJak3/WT $\gamma_c$, Jak3 Y100C/WT $\gamma_c$, WT Jak3/P266, 269A $\gamma_c$, or WT Jak3/ P266, 269G $\gamma_c$. Lysates from these cells were immunoprecipitated with anti-FLAG monoclonal antibody M2, and blots were probed with rabbit polyclonal anti-Jak3 antibody. In other experiments, Myc-tagged Jak3 fragment 1–193 was coexpressed in 293T cells with WT $\gamma_c$ or the Box 1 mutants of $\gamma_c$. Lysates were immunoprecipitated with goat polyclonal anti-$\gamma_c$ antibody, and blots were probed with anti-Myc tag monoclonal antibody 9E10.

The results demonstrated that although equal levels of Jak3 and $\gamma_c$ were expressed in the transfected cells, the P266, 269A or P266, 269G mutations reduced the interaction of $\gamma_c$ with full-length Jak3 to barely detectable levels. Furthermore, these $\gamma_c$ box1 proline mutations also reduced the interaction of $\gamma_c$ with a Jak3 fragment containing the amino-terminal portion of Jak3.

The Myc-tagged fragment of Jak3, encoding amino acids 1–193 interacted strongly with WT $\gamma_c$ but only very weakly with the P266, 269A or P266, 269G mutants of $\gamma_c$. These results confirmed the findings obtained with full-length Jak3 and further demonstrated a direct interaction between the amino-terminus of Jak3 and the proline-rich box1 region of $\gamma_c$.

These results show that mutation of the box1 proline residues 266 and 269 markedly reduces $\gamma_c$ binding to Jak3 and further indicate that this box1 region specifically interacts with the JH6/JH7 regions of Jak3. This data clearly suggests that the Janus kinases most likely interact with receptor box1 motifs through a sequence overlapping JH6/JH7 and that the specificity of the Jak kinase interaction is mostly contained within this region.

VII. Binding of $\gamma_c$ with Jak3/Jak1 chimeras.

To further define which region of the amino-terminus of Jak3 was required for specific functional receptor association, a series of staggered chimeras between Jak3 and Jak1 was generated. The ability of the Jak3/Jak1 chimeras to associate with the $\gamma_c$ receptor chain was examined by immunoprecipitating the epitope-tagged chimeric Jak proteins, and blotting for $\gamma_c$ from lysates of transfected 293T cells.

Six Jak3/Jak1 chimeras were generated as follows: J3 1–109 (which encodes JH7 minus 10 amino acids of Jak3); J3 1–130 (which encodes JH7 plus 5 amino acids of JH6 of Jak3); J3 1–193 (which encodes JH7 plus 73 amino acids of JH6 of Jak3); J3 1–256 (which encodes JH7–JH6); J3 1–300 (which encodes JH7–JH5, plus 10 residues of JH4 of Jak3; JH4–JH1 of Jak1); and J3 1–519 (which encodes the JH7–JH3 of Jak3 and JH1 and JH2 of Jak1). Lysates from 293T cells coexpressing $\gamma_c$ and the Jak3/Jak1 chimeras were immunoprecipitated with Sepharose-conjugated M2 anti-FLAG monoclonal antibody, and blots were probed with rabbit polyclonal anti-$g_c$ antibody.

When compared to WT Jak3, the J3 1–109 chimera, containing a carboxy-terminal truncation of the receptor interaction domain, failed to bind $\gamma_c$. This finding supports Jak3 truncation experiments and suggests that the region which encodes JH7 minus 10 amino acids of Jak3 is not sufficient to mediate $\gamma_c$ binding.

The J3 1–130 chimera, encoding JH7 plus 5 amino acids of JH6, interacted weakly with $\gamma_c$ although, the J3 1–193, J3 1–256, J3 1–300, and J3 1–519 chimeras all interacted comparable to WT Jak3. These results indicate that the amino-terminal region containing all of JH7 and the first five amino acids of JH6 is sufficient to permit $\gamma_c$ binding, but that binding is enhanced as more of the Jak3 amino-terminus is added.

VIII. Tyrosine Phosphorylation of Jak3/Jak1 chimeras after IL-2 stimulation.

Interaction of Jak3 with its cognate receptor is known to be required for functioning IL-2 responses. Therefore, the ability of the Jak3/Jak1 chimeras to signal in response to IL-2 stimulation was examined.

Jak3/Jak1 chimeras were introduced, by retroviral transduction, into fibroblasts that express the IL-2 receptor (IL-2R+) but not Jak3. Specifically, IL-2R+ fibroblasts lacking Jak3 were transfected for stably expressing: WT Jak3; the J3 1–130 chimera, the J3 1–193 chimera; or the J3 1–256 chimera.

The resulting stably expressing cells were stimulated with 1000 U/ml IL-2 for approximately 15 min. The cells were then lysed as described above, and epitope-tagged wild-type Jak3 or J3/J1 chimeras from the lysates were immunoprecipitated with rabbit polyclonal anti-FLAG antibody onto blots. Subsequently, the blots were probed with anti-phosphotyrosine monoclonal antibody 4G10 to determine if tyrosine phosphorylation of Jak3 or the J3/J1 chimeras had occurred.

The J3 1–109 (JH7 minus 10 amino acids of Jak3) which contains the minimal receptor interaction domain was not tyrosine-phosphorylated in response to IL-2, nor was a longer chimera containing 60 additional amino acids at the C-terminus.

The smallest region of a chimeric Jak3/Jak1 which reconstituted IL-2-induced tyrosine phosphorylation was a region that contained both of the entire JH7 and JH6 domains, a region considerably larger than the minimal receptor binding domain defined in coexpression studies (i.e., the amino-terminal region of the entire JH7 and the first five amino acids of JH6).

Further evidence of the ability of the JH7/JH6 chimera to reconstitute IL-2-inducible responses was demonstrated by phosphorylation of the IL-2 receptor beta chain (IL-2Rβ), which is co-precipitated along with the JH7/JH6 chimera. Phosphorylation of IL-2Rβ is a hallmark indicator of a functioning IL-2 response and it was only detected in cell lines that expressed Jak3/Jak1 chimeras having the entire JH7 and JH6 domains.

IX. STAT5b Phosphorylation of Jak3/Jak1 chimeras after IL-2 stimulation.

To further test the ability of the Jak3/Jak1 chimeras to reconstitute a functional IL-2 response, the phosphorylation of transiently expressed STAT5b was examined.

IL-2R+ fibroblasts transiently expressing STAT5b and lacking Jak3 or expressing WT Jak3 or Jak3/Jak1 chimeras J3-130, or J3 1–270 were stimulated with IL-2 and lysed as described above. Lysates were immunoprecipitated with rabbit polyclonal anti-STAT5b antibody and blots were probed with anti-phosphotyrosine monoclonal antibody 4G10.

Cells expressing wild type Jak3 (WT) exhibited tyrosine phosphorylation of STAT5b. Non-Jak3 expressing cells showed no STAT5b tyrosine phosphorylation. Moreover, cells expressing the J3 1–130 chimera also failed to demonstrate STAT5b phosphorylation suggesting that this region of Jak3 is not sufficient to elicit downstream responses following IL-2 stimulation. However, consistent with results showing phosphorylation of IL-2β, the J3 1–256 chimera (encoding both of the entire JH7/JH6 regions) responded to IL-2 stimulation by tyrosine phosphorylating STAT5b.

These data are consistent with a model in which the complete JH7 and JH6 domains of Jak3 are sufficient for functional reconstitution of IL-2-induced responses.

Although the amino terminal JH6/JH7 domains of Jaks have been shown to interact with receptors in coexpression studies, it has been suggested that JH7–JH3 are required to mediate cytokine-induced signaling responses. For example, the JH3-JH7 domains of Tyk2 are required for stabilization of IFNαR1 expression. Gauzzi, et al. (1997) *Proc. Nat'l Acad. Sci. USA* 94:11839–11844. In addition, studies with chimeric kinases have shown that IFNγ-induced STAT1 activation was dependent on JH6/JH7 domains of Jak2, while all of the JH3–JH7 domains of Jak1 were required to reconstitute STAT1 activation. Kohlhuber, et al. (1997) *Mol. Cell. Biol.* 17:695–706. Likewise, it has been demonstrated that the JH4–JH7 domains of Jak3 are sufficient to induce signaling events in response to IL-2. Chen, et al. (1997) *Proc. Nat'l Acad. Sci. USA* 94:6910–6915.

The teachings herein show that a minimal functional receptor interaction domain of Jak3 (JH6/JH7; amino acids 1–256) mediates $\gamma_c$ binding and reconstitutes biochemical signaling in response to IL-2 stimulation. In addition, the teachings of the present invention show that Jak3/Jak1 chimeras containing only Jak3 residues 1–130 or 1–193 can bind $\gamma_c$ but do not elicit downstream signaling events in response to cytokine stimulation. This suggests that while amino acid residues 1–130 (i.e., JH7 plus 5 amino acids of JH6) can bind $\gamma_c$, residues 1–256 (or the complete JH6/JH7 domains) are required for IL-2-induced Jak3 activation and induction of STAT5 tyrosine phosphorylation. Therefore, while the complete JH6/JH7 domains are not required for $\gamma_c$ receptor interaction, they are necessary for enhancing Jak activation and subsequent downstream signaling.

Several autosomal SCID patients who express Jak3 protein have Jak3 mutations that result in constitutive tyrosine phosphorylation of the kinase, and in each case, cytokine-induced responses are impaired. Candotti, et al. (1998) *Springer Semin. Immunopathol.* 19:401–415. The single amino acid substitution of Jak3 described herein (YL100C) also results in a loss of proper regulation of basal tyrosine phosphorylation.

These discoveries raise the possibility that the activity or basal tyrosine phosphorylation state of Jak kinases may be regulated by intramolecular interactions, similar to Tec and Src-family kinases. Andreotti, et al. (1997) *Nature* 385:93–97; and Moarefi, et al. (1997) *Nature* 385:650–653. Autosomal SCID point mutations and deletions may disrupt a regulatory interaction that controls basal phosphorylation state of the molecule, resulting in the constitutive phosphorylation in cells derived from the patients, and possibly contributing to the SCID phenotype. However, the inability of Jak3 Y100C to interact with $\gamma_c$ is not due to its constitutive phosphorylation, as has been demonstrated by the failure of the kinase-inactive derivative, Jak3 Y100C/K855A, to interact with $\gamma_c$ in 293T cells.

The fact that a Jak3/Jak1 chimeric kinase can functionally substitute for Jak3 in the IL-2 receptor complex, suggests that the Jak1 catalytic domain can efficiently induce tyrosine phosphorylation of the IL-2Rβ chain and STAT5 in the absence of Jak3 catalytic activity. The teachings herein suggest that the specificity of cytokine responses is not dependent on the catalytic domain of the receptor-associated Jak kinase. Therefore, while the initiation of cytokine responses requires correct targeting of a Jak kinase catalytic domain to the receptor complex, the substrate specificity of the kinase does not appear to play a major role in the cytokine signaling response.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated polynucleotide encoding:
   a) a polypeptide that comprises an amino acid sequence that differs from SEQ ID NO: 1 by one or two point mutations at amino acid residues L98 and I102; or
   b) a fragment of said polypeptide, said fragment comprising said point mutations;
      wherein said point mutations result in the loss of IL-2-induced tyrosine phosphorylation of said polypeptide or its interaction with the common gamma chain ($\gamma_c$).

2. The polynucleotide of claim 1, wherein said fragment comprises portions of the JH7 and JH6 domains selected from the group consisting of amino acid residues 1–130, 1–193, 1–256, 70–130, and 70–193 of SEQ ID NO: 1.

3. The polynucleotide of claim 1, wherein said point mutations are L98A and I102A.

4. An isolated polynucleotide encoding
   a) a polypeptide comprising an amino acid sequence that differs from SEQ ID NO: 1 by a Y100A point mutation; or
   b) a fragment of said polypeptide, said fragment comprising said point mutation.

5. The polynucleotide of claim 1, wherein the amino acid sequence differs from SEQ ID NO: 1 by a point mutation at L98.

6. The polynucleotide of claim 5, wherein the point mutation is L98A.

7. The polynucleotide of claim 1, wherein the amino acid sequence differs from SEQ ID NO: 1 by a point mutation at I102.

8. The polynucleotide of claim 7, wherein the point mutation is I102A.

9. The polynucleotide of claim 1, wherein the amino acid sequence differs from SEQ ID NO: 1 by point mutations at L98 and I102.

10. The polynucleotide of claim 9, wherein the point mutations are L98A and I102A.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1124 amino acids
      (B) TYPE: amino acid
      (C) STRANDEDNESS: Not Relevant
      (D) TOPOLOGY: linear (ii) MOLECULE TYPE: peptide (ix) FEATURE:
    (A) NAME/KEY: CDS
    (B) LOCATION: 1..1062

(xi) SEQUENCE DESCRIPTION: SEQ ID NO:1:

```
Met Ala Pro Pro Ser Glu Thr Pro Leu Ile Pro Gln Arg Ser Cys
1               5                   10                  15

Ser Leu Leu Ser Thr Glu Ala Gly Ala Leu His Val Leu Leu Pro Ala
                20                  25                  30

Arg Ala Pro Gly Pro Pro Gln Arg Leu Ser Phe Ser Phe Gly Asp His
                35                  40                  45

Leu Ala Glu Asp Leu Cys Val Gln Ala Ala Lys Ala Ser Gly Ile Leu
        50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
                100                 105                 110

Glu Lys Cys His Arg Phe Gly Leu Arg Lys Asp Leu Ala Ser Ala Ile
                115                 120                 125

Leu Asp Leu Pro Val Leu Glu His Leu Phe Ala Gln His Arg Ser Asp
        130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
                180                 185                 190

Cys Leu Pro Pro Ser Leu Arg Asp Leu Ile Gln Gly Leu Ser Phe Val
                195                 200                 205

Thr Arg Arg Ala Ile Arg Arg Thr Val Arg Arg Ala Leu Pro Arg Val
        210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
                260                 265                 270

Val Ala Gly Asp Gly Gly Ile Ala Trp Thr Gln Gly Glu Gln Glu Val
        275                 280                 285

Leu Gln Pro Phe Cys Asp Phe Pro Glu Ile Val Asp Ile Ser Ile Lys
        290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
                340                 345                 350

Thr Asp Ser Gln His Phe Phe Cys Lys Glu Val Ala Pro Pro Arg Leu
        355                 360                 365

Leu Glu Glu Val Ala Glu Gln Cys His Gly Pro Ile Thr Leu Asp Phe
370                 375                 380
```

-continued

```
Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
            405                 410                 415

Val Gln Asn Pro Leu Gly Pro Asp Tyr Lys Gly Cys Leu Ile Arg Arg
            420                 425                 430

Ser Pro Thr Gly Thr Phe Leu Leu Val Gly Leu Ser Arg Pro His Ser
        435                 440                 445

Ser Leu Arg Glu Leu Leu Ala Thr Cys Trp Asp Gly Leu His Val
    450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
            500                 505                 510

Phe His Lys Ile Pro Ala Asp Ser Leu Glu Trp His Glu Asn Leu Gly
        515                 520                 525

His Gly Ser Phe Thr Lys Ile Tyr Arg Gly Cys Arg His Glu Val Val
    530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
            580                 585                 590

Ala Gly Asp Ser Thr Met Val Gln Glu Phe Val His Leu Gly Ala Ile
        595                 600                 605

Asp Met Tyr Leu Arg Lys Arg Gly His Leu Val Pro Ala Ser Trp Lys
    610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
        675                 680                 685

Pro Trp Val Ala Pro Glu Cys Leu Arg Glu Ala Gln Thr Leu Ser Leu
    690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
                725                 730                 735

Phe Tyr Glu Asp Arg Gln Gln Leu Pro Ala Pro Lys Trp Thr Glu Leu
            740                 745                 750

Ala Leu Leu Ile Gln Gln Cys Met Ala Tyr Glu Pro Val Gln Arg Pro
        755                 760                 765

Ser Phe Arg Ala Val Ile Arg Asp Leu Asn Ser Leu Ile Ser Ser Asp
    770                 775                 780

Tyr Glu Leu Leu Ser Asp Pro Thr Pro Gly Ala Leu Ala Pro Arg Asp
785                 790                 795                 800
```

```
Gly Leu Trp Asn Gly Ala Gln Leu Tyr Ala Cys Gln Asp Pro Thr Ile
            805                 810                 815

Phe Glu Glu Arg His Leu Lys Tyr Ile Ser Gln Leu Gly Lys Gly Asn
            820                 825                 830

Phe Gly Ser Val Glu Leu Cys Arg Tyr Asp Pro Leu Ala His Asn Thr
            835                 840                 845

Gly Ala Leu Val Ala Val Lys Gln Leu Gln His Ser Gly Pro Asp Gln
            850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Pro
            885                 890                 895

Glu Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
            915                 920                 925

Tyr Ser Ser Gln Ile Cys Lys Gly Met Glu Tyr Leu Gly Ser Arg Arg
            930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
            965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
            995                 1000                1005

Asp Val Trp Ser Phe Gly Val Val Leu Tyr Glu Leu Phe Thr Tyr Cys
            1010                1015                1020

Asp Lys Ser Cys Ser Pro Ser Ala Glu Phe Leu Arg Met Met Gly Cys
1025                1030                1035                1040

Glu Arg Asp Val Pro Ala Leu Cys Arg Leu Leu Glu Leu Leu Glu Glu
            1045                1050                1055

Gly Gln Arg Leu Pro Ala Pro Pro Ala Cys Pro Ala Glu Val His Glu
            1060                1065                1070

Leu Met Lys Leu Cys Trp Ala Pro Ser Pro Gln Asp Arg Pro Ser Phe
            1075                1080                1085

Ser Ala Leu Gly Pro Gln Leu Asp Met Leu Trp Ser Gly Ser Arg Gly
            1090                1095                1100

Cys Glu Thr His Ala Phe Thr Ala His Pro Glu Gly Lys His His Ser
1105                1110                1115                1120

Leu Ser Phe Ser (2) INFORMATION FOR SEQ ID NO:2:

(i) SEQUENCE CHARACTERISTICS:
        (A) LENGTH: 369 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: CDS
        (B) LOCATION: 1..1062
```

(xi) SEQUENCE DESCRIPTION: SEQ ID NO:2:

```
Met Leu Lys Pro Ser Leu Pro Phe Thr Ser Leu Leu Phe Leu Gln Leu
 1               5                  10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
            85                  90                  95

Asp Lys Val Gln Lys Cys Ser His Tyr Leu Phe Ser Glu Glu Ile Thr
        100                 105                 110

Ser Gly Cys Gln Leu Gln Lys Lys Glu Ile His Leu Tyr Gln Thr Phe
    115                 120                 125

Val Val Gln Leu Gln Asp Pro Arg Glu Pro Arg Arg Gln Ala Thr Gln
130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
            165                 170                 175

Arg Phe Leu Asn His Cys Leu Glu His Leu Val Gln Tyr Arg Thr Asp
        180                 185                 190

Trp Asp His Ser Trp Thr Glu Gln Ser Val Asp Tyr Arg His Lys Phe
    195                 200                 205

Ser Leu Pro Ser Val Asp Gly Gln Lys Arg Tyr Thr Phe Arg Val Arg
210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
            245                 250                 255

Leu Phe Ala Leu Glu Ala Val Val Ile Ser Val Gly Ser Met Gly Leu
        260                 265                 270

Ile Ile Ser Leu Leu Cys Val Tyr Phe Trp Leu Glu Arg Thr Met Pro
    275                 280                 285

Arg Ile Pro Thr Leu Lys Asn Leu Glu Asp Leu Val Thr Glu Tyr His
290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
            325                 330                 335

Pro Lys Gly Gly Ala Leu Gly Glu Gly Pro Gly Ala Ser Pro Cys Asn
        340                 345                 350

Gln His Ser Pro Tyr Trp Ala Pro Pro Cys Tyr Thr Leu Lys Pro Glu
    355                 360                 365

Thr
```